(12) United States Patent
Beard et al.

(10) Patent No.: US 9,849,012 B2
(45) Date of Patent: Dec. 26, 2017

(54) PORT RETENTION MECHANISM FOR DEPLOYMENT HANDLE OF A MEDICAL DEVICE DEPLOYMENT SYSTEM

(71) Applicant: W. L. Gore & Associates, Inc., Newark, DE (US)

(72) Inventors: Matthew S. Beard, Phoenix, AZ (US); David A. Herrin, Seattle, WA (US); Joseph N. Kennelly Ullman, Seattle, WA (US); Martin J. Sector, Gilbert, AZ (US); Justin W. Sokel, Flagstaff, AZ (US); Jared L. Van Cleave, Kirkland, WA (US)

(73) Assignee: W. L. Gore & Associates, Inc., Newark, DE (US)

( * ) Notice: Subject to any disclaimer, the term of this patent is extended or adjusted under 35 U.S.C. 154(b) by 305 days.

(21) Appl. No.: 14/677,739

(22) Filed: Apr. 2, 2015

(65) Prior Publication Data

US 2015/0282965 A1    Oct. 8, 2015

Related U.S. Application Data

(60) Provisional application No. 61/975,197, filed on Apr. 4, 2014.

(51) Int. Cl.
*A61F 2/95* (2013.01)
*A61F 2/962* (2013.01)
*A61F 2/966* (2013.01)

(52) U.S. Cl.
CPC ............... *A61F 2/95* (2013.01); *A61F 2/962* (2013.01); *A61F 2002/9517* (2013.01); *A61F 2002/9665* (2013.01)

(58) Field of Classification Search
CPC .... A61F 2/95; A61F 2/962; A61F 2002/9665; A61F 2002/9517
USPC ........................................................ 604/533
See application file for complete search history.

(56) References Cited

U.S. PATENT DOCUMENTS

| | | | |
|---|---|---|---|
| 4,631,056 A * | 12/1986 | Dye | A61M 39/1011 285/3 |
| 6,352,561 B1 | 3/2002 | Leopold et al. | |
| 6,551,350 B1 | 4/2003 | Thornton et al. | |
| 7,799,015 B2 * | 9/2010 | Schweikert | A61M 39/1011 24/522 |
| 2003/0144670 A1 * | 7/2003 | Pavcnik | A61F 2/2436 606/108 |
| 2010/0049293 A1 | 2/2010 | Zukowski et al. | |
| 2013/0085562 A1 | 4/2013 | Rincon et al. | |

* cited by examiner

*Primary Examiner* — Julian W Woo

(57) ABSTRACT

A catheter assembly includes a tubular first and second catheters in fluid communication with each other, wherein the second catheter includes a port fitting and can be elastically longitudinally strained to cinch the first and second catheters together.

13 Claims, 10 Drawing Sheets

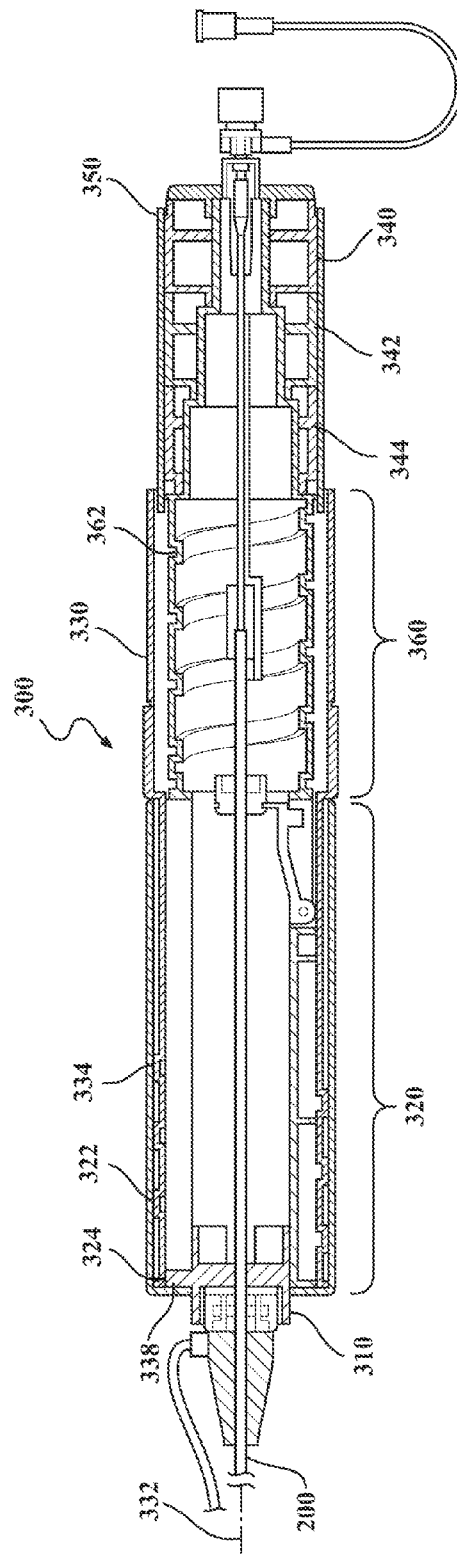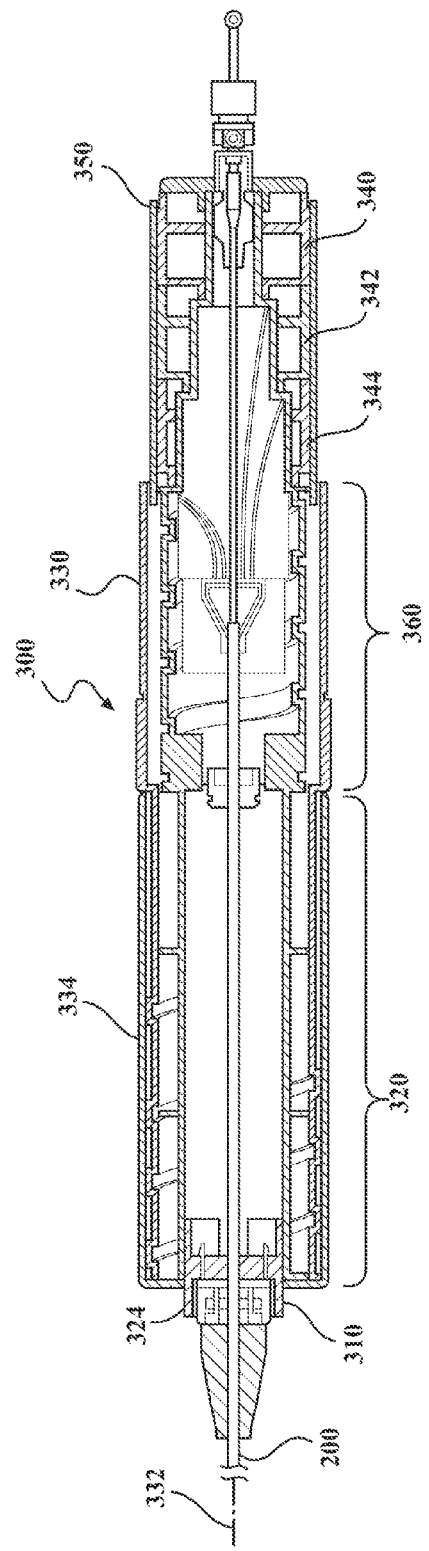

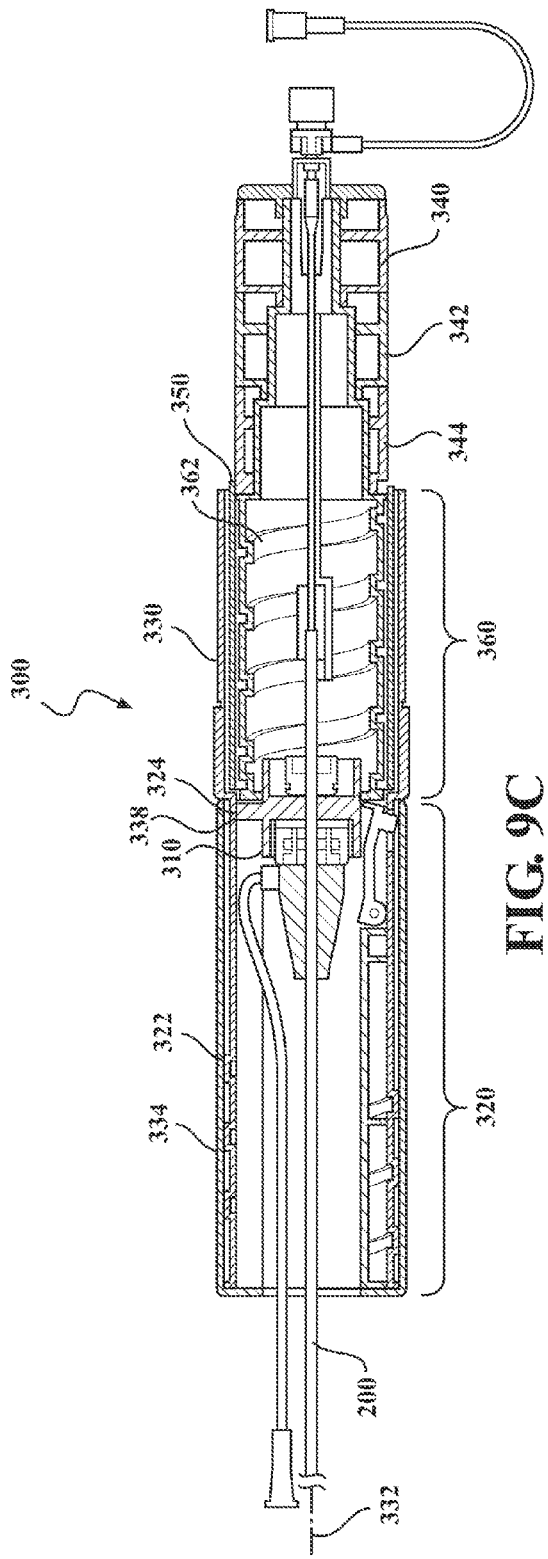
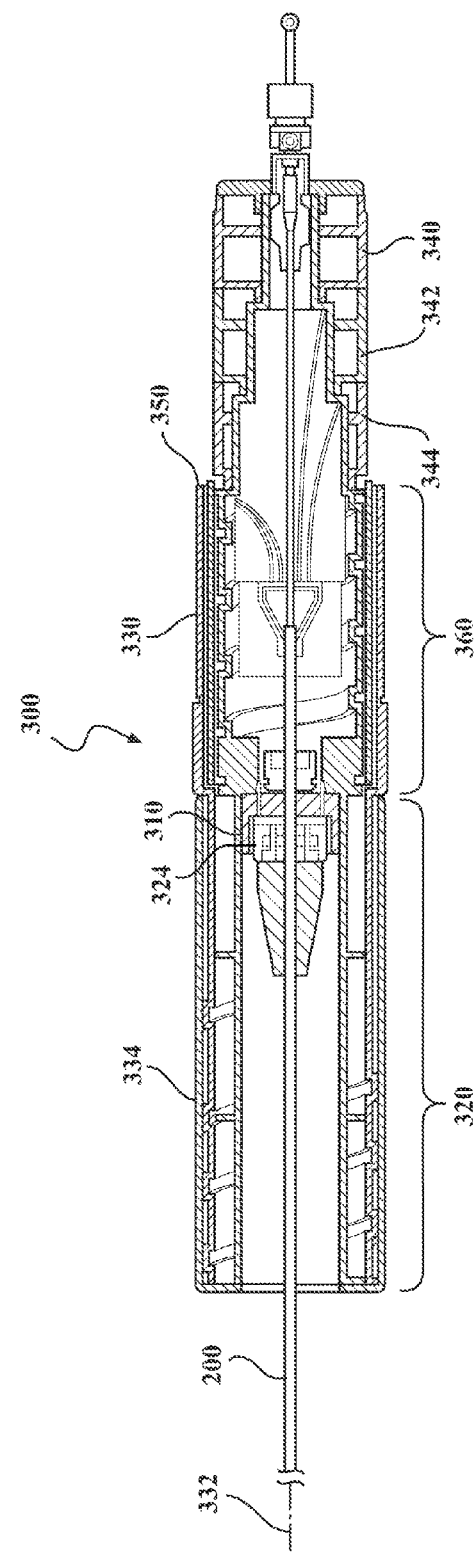
FIG. 9C
FIG. 9D

PORT RETENTION MECHANISM FOR DEPLOYMENT HANDLE OF A MEDICAL DEVICE DEPLOYMENT SYSTEM

BACKGROUND

Field

The present disclosure relates to medical device deployment systems. More particularly, the present disclosure relates to a handle for a medical device deployment system.

Discussion of the Related Art

There is a need for advanced devices, tools, systems and methods used for the endoluminal treatment of aortic diseases. In particular, there remains a need for deployment systems that can accommodate increasingly complex modes of deployment of a device, such as steering, reconstraining, multiple stage deployment, multiple device deployment, while promoting ease of use to the clinician.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

FIGS. 9A and 9B are top and front elevational views, respectively, of a handle of the introducer assembly in a first state.

FIGS. 9C and 9D are top and front elevational views, respectively, of a handle of the introducer assembly in a second state.

DETAILED DESCRIPTION

Introducer assemblies for endoluminal delivery of vascular implants in accordance with various embodiments are disclosed for allowing actuation or deployment of a vascular implant, while forcing a particular order of operation of the handle by a clinician.

Figure 1:
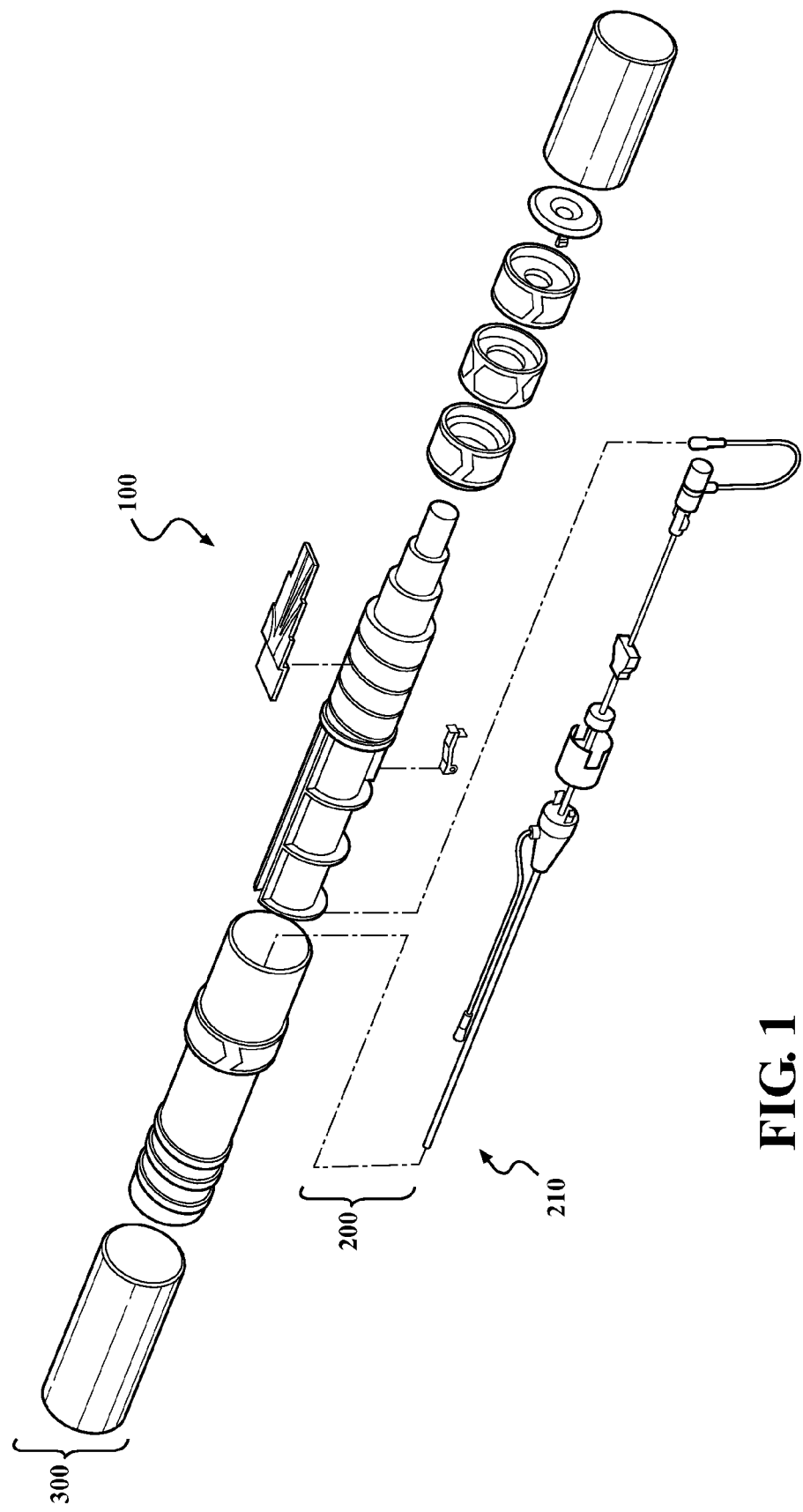
FIG. 1 is an exploded perspective view of an introducer assembly in accordance with the present disclosure.

In various embodiments, an introducer assembly includes a first actuating mechanism for actuating a constraining sheath between a first state releasably constraining a vascular implant and a second state allowing deployment of the vascular implant; a second actuating mechanism for actuating a blocking mechanism between a blocked state for blocking one or more other knobs and/or other functions of the handle and an unblocked state for allowing operation of the one or more other knobs and/or other functions of the handle; and an operating knob operatively coupled to both of the first and second actuating mechanisms for concurrent operation of both of the first and second actuating mechanisms in response to actuation of the operating knob. An example of such an introducer assembly is generally indicated at 100 in FIG. 1. The introducer assembly 100 includes a sheath 200 and a handle 300. The introducer assembly 100 includes a constraint (not shown) for releasably constraining a vascular implant toward a distal end 210 of the sheath 200. The constraint has a first state releasably constraining an expandable implant toward a delivery configuration suitable for endoluminal delivery, and a second state released to allow expansion of the implant from the delivery configuration toward a deployed configuration. The handle includes an actuating member operatively coupled to the constraint for actuating the constraint between the first state and the second state.

In various embodiments, the constraint can include a film sleeve that extends around the implant. In the first state, opposite portions or edges of the film sleeve can be releasably held or sewn together by an elongated member, such as a wire or fiber, to maintain the implant in the delivery configuration. In such embodiments, the sleeve can be opened, or otherwise disrupted, by displacing, unstitching or otherwise disengaging the elongated member from the film sleeve to allow expansion of the implant. Further details of such constraining sleeves can be found, for example, U.S. Pat. No. 6,352,561 issued to Leopold, et al., and U.S. Pat. No. 6,551,350 issued to Thornton, et al., the content of which is incorporated herein by reference in its entirety. In such embodiments, the actuating member can be coupled to the elongated member to release or open the film sleeve from the first state to the second state.

In other embodiments, the constraint can include an axially displaceable tube, wherein such a tube can be formed from a wrapped film tube or an extruded polymer. Indeed, in various embodiments, the sheath itself could be such a constraint, wherein the sheath in the first state extends over the implant to retain the implant toward the delivery configuration. The sheath can be displaced toward the second state to allow expansion of the implant from the delivery configuration. In such embodiments, the actuating member can be coupled to the sheath so that the sheath is displaced with the actuating member between the first state and second state.

Thus, the actuating member can be configured for deploying an implant from either type of constraint described above, or other similarly actuated constraint mechanisms known in the art. The latter type of integrated sheath and constraint are described below in connection with the illustrated embodiments.

Referring to FIGS. 9A-9D, the handle 300 includes an actuating member 310 coupled to the sheath 200 for actuating the sheath 200 between the first state and second state in response to linear displacement of the actuating member 310 between a first position and a second position, respectively. The handle 300 includes a first actuating mechanism 320 for displacing the actuating member 310 between the first position and the second position.

The handle 300 includes a main knob 330 for operating the first actuating mechanism 320. Described further below, the handle 300 can include one or more additional knobs to operate one or more additional separate handle functions. The handle 300 includes a cover 350 operable for movement between a covered state covering the one or more additional knobs 340, 342, 344 as shown in FIGS. 9A and 9B, and an uncovered state allowing access to the one or more additional knobs 340, 342, 344 as shown in FIGS. 9C and 9D. The handle 300 includes a second actuating mechanism 360 for displacing the cover 350 between the covered state and the uncovered state. The main knob 330 is operatively coupled to both of the first actuating mechanism 320 and the second actuating mechanism 360 to cause displacement of both the actuating member 310 between the first state and the second state and the cover 350 between the covered state and the uncovered state, respectively, in response to corresponding operation of the main knob 330.

Figure 10:
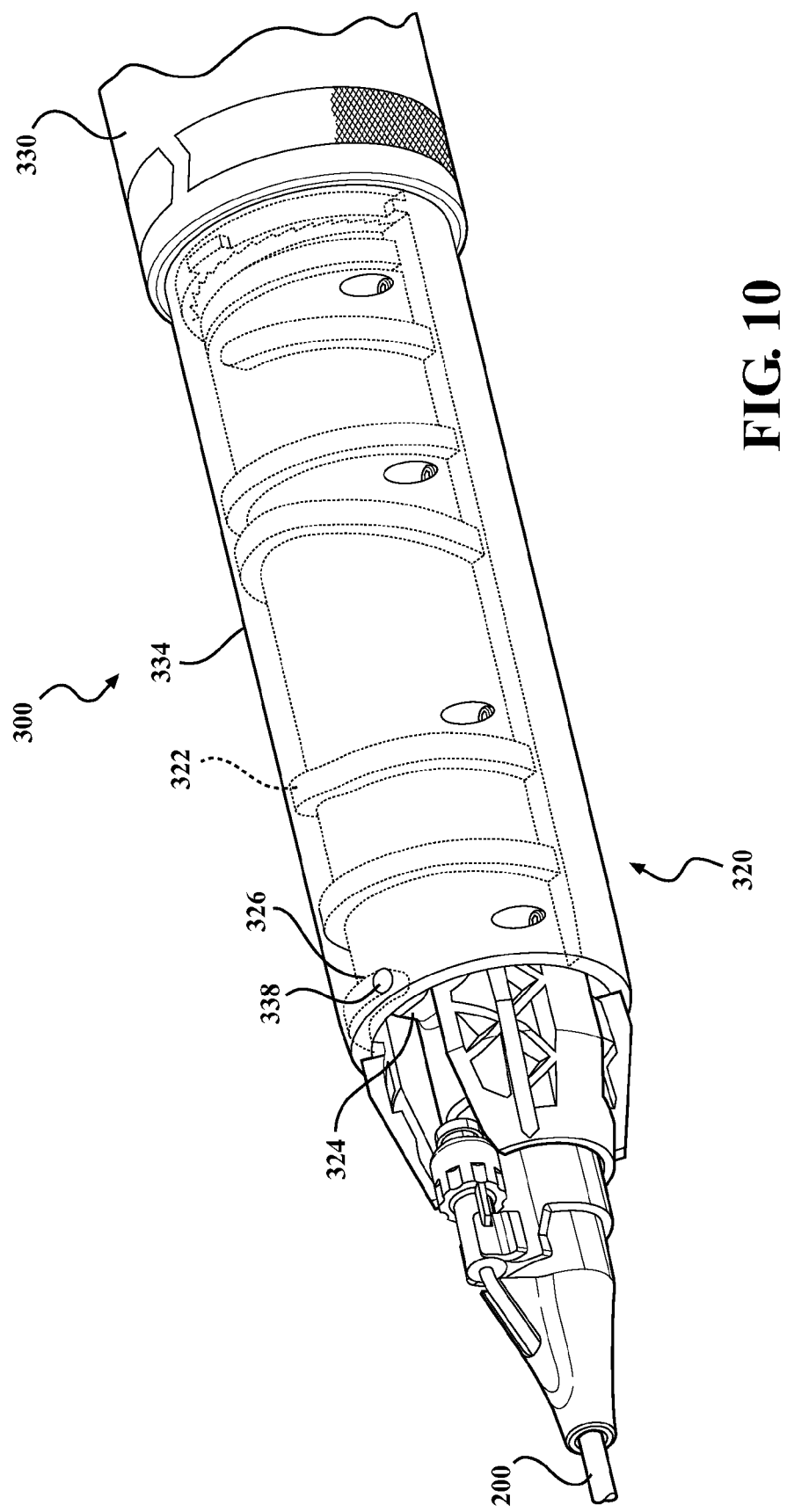
FIG. 10 is a perspective view of a front portion of the introducer assembly.
Figure 11:
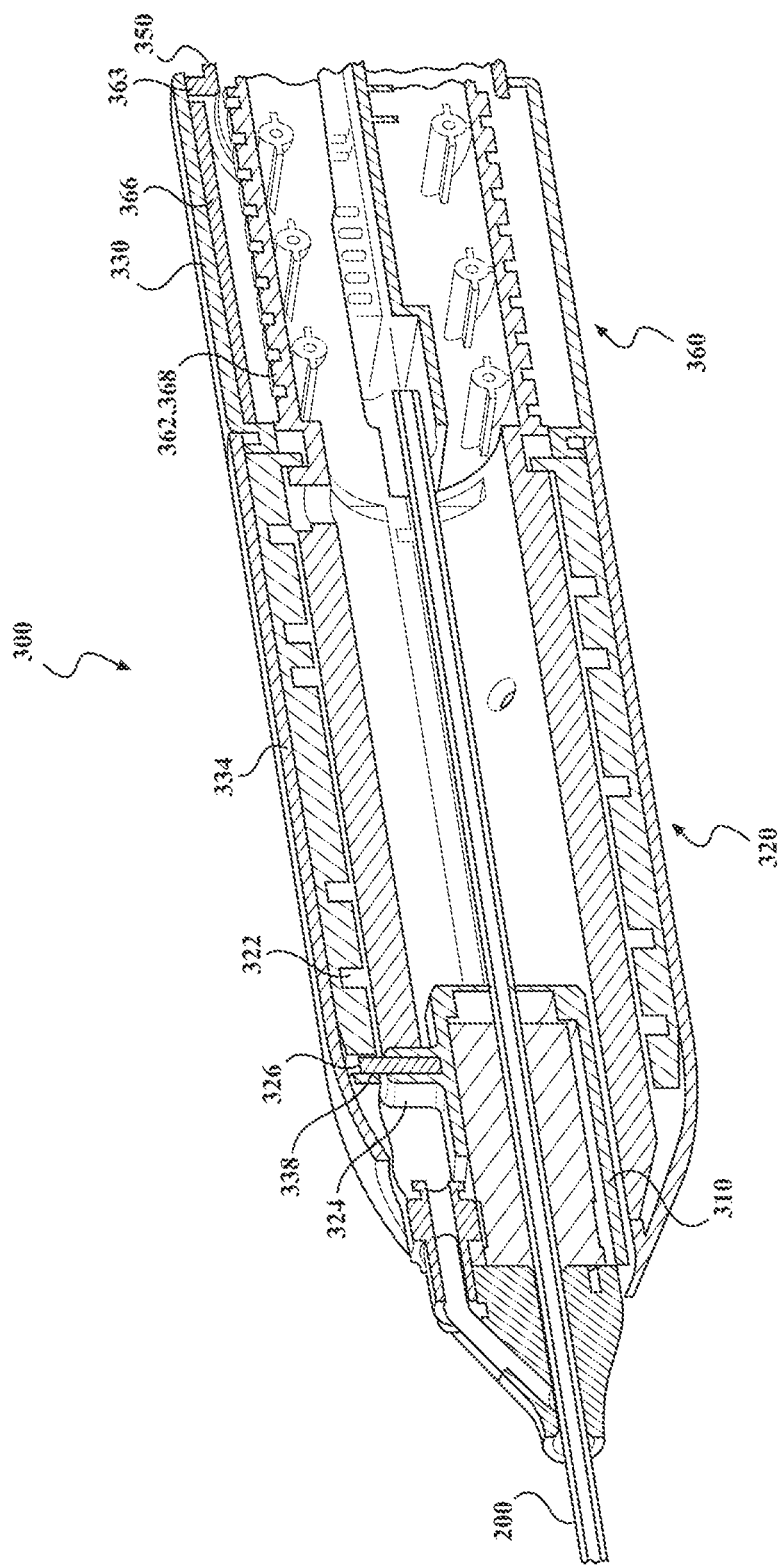
FIG. 11 is a cross-sectional view of a front portion of the introducer assembly.

In various embodiments, an actuating knob of the handle can be configured for rotation about an axis, and an actuating member for actuating one or more functions of the handle can be configured for displacement along and/or about the axis between operating states in response to corresponding rotation of the actuating knob. For example, as shown in FIGS. 9A-9D, the main knob 330 is rotatable about a rotational axis 332. The actuating member 310 is movable linearly along the axis 332 between the first state and second state. Referring to FIGS. 10 and 11, the first actuating mechanism 320 includes a first helical guide 322 movable with the main knob 330 about the axis 332. The first actuating mechanism 320 includes a first follower 324 on the actuating member 310 engaged with the first helical guide 322 to cause linear movement of the actuating member 310 between the first state and second state in response to corresponding rotation of the main knob 330. The main knob 330 includes a receiving tube 334 receiving at least a portion of the actuating member 310 therethrough as the actuating member 310 moves between the first state and second state. In a number of embodiments, the first helical guide 322 is a first helical slot 326 formed along an inner surface 336 of the receiving tube 334 and the first follower 324 includes an outwardly extending first pin 338 engaged with the helical slot 326.

Figure 12:
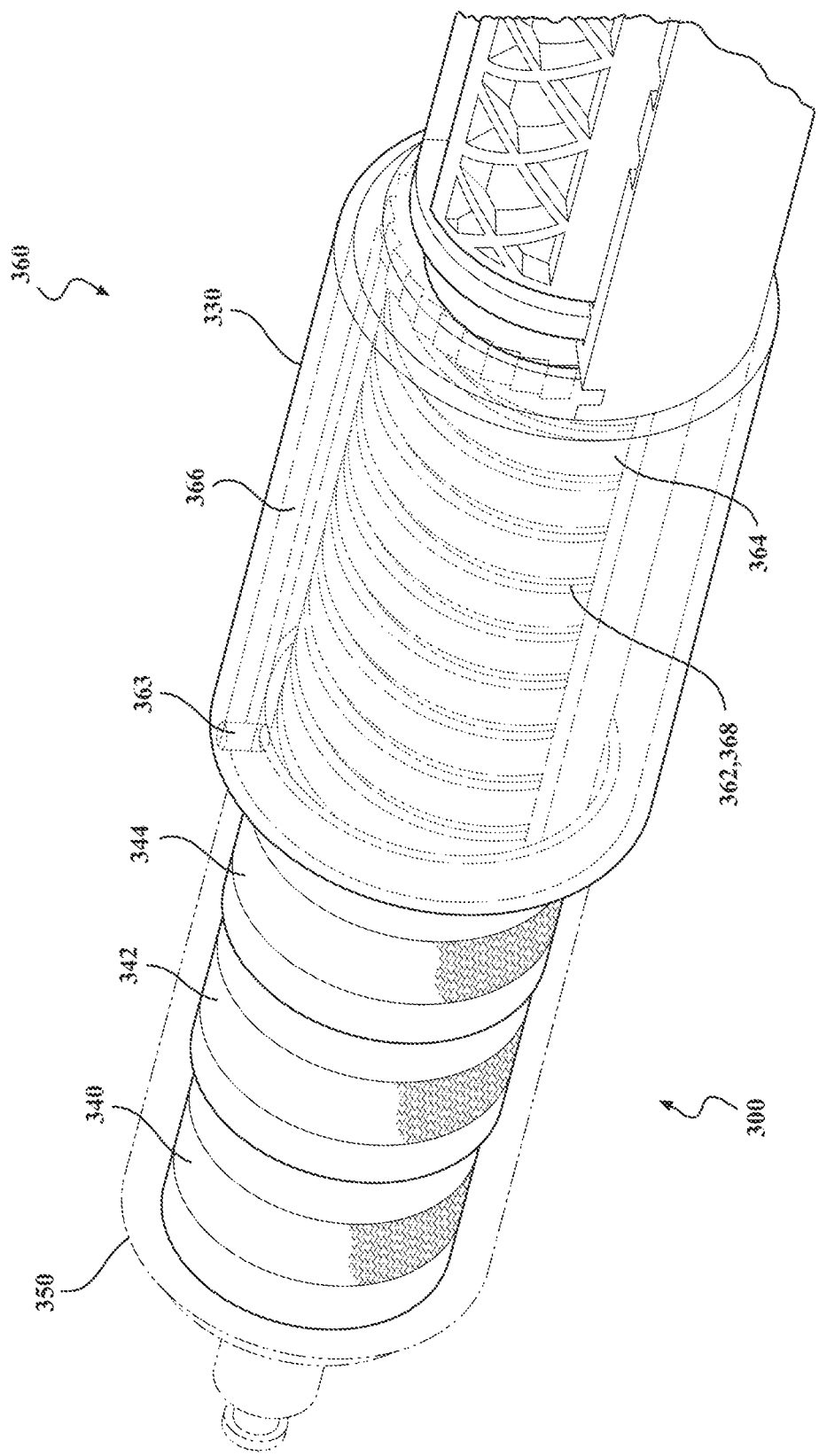
FIG. 12 is a perspective view of a rear portion of the introducer assembly.
Figure 13:
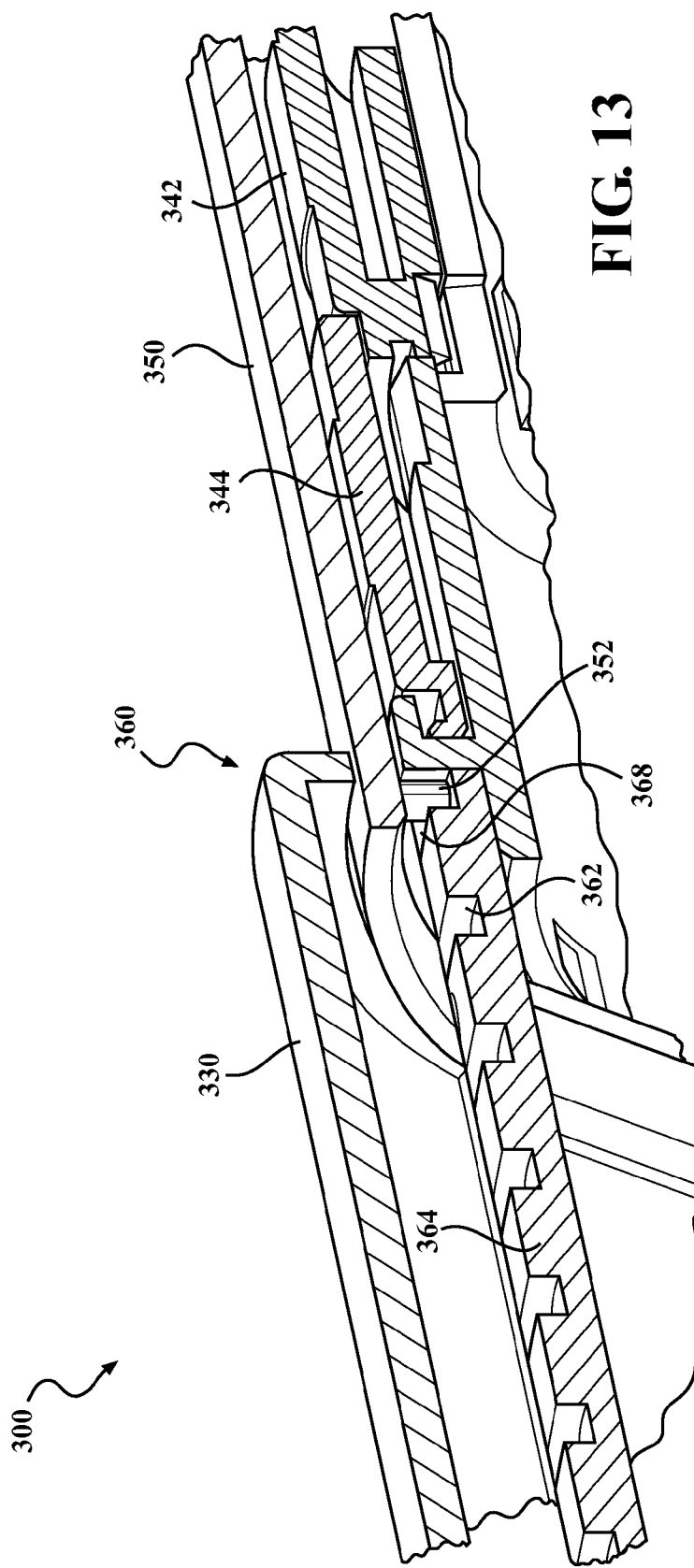
FIG. 13 is a cross sectional view of a rear portion of the introducer assembly.

Referring to FIG. 12, the second actuating mechanism 360 includes a second helical guide 362 that translates rotation of the main knob 330 to axial displacement of the cover 350. In one embodiment, the second helical guide 362 comprises a second helical slot 368 formed along an outer surface 366 of a spindle 364, the spindle 364 being aligned with the axis 332 of the main knob 330. The second actuating mechanism 360 also includes a longitudinal slot 366 formed along the main knob 330. In various embodiments, the slot 366 is parallel with the axis 332 of the main knob 330. The second actuating mechanism 360 includes a second pin 363 extending from the cover 350 and slidably engaged with the longitudinal slot 366. As best shown in FIG. 13, the second actuating mechanism 360 includes a third pin 352 extending from the cover 350 and engaging the second helical slot 368 to cause displacement of the cover 350 between the covered state and the uncovered state in response to corresponding rotation of the main knob 330.

The actuating mechanisms of the handle can be configured so that functions, such as displacements of the actuating member and cover, are delayed or accelerated relative to each other during operation of the main knob. For example, the first helical guide can include a flat or reduced or increased pitch to cause a delay, decrease or increase, respectively, in the displacement of the actuating mechanism relative to the cover in response to operation of the main knob.

In various embodiments, the handle can include a ratchet mechanism that allows actuation of an actuating knob in a first direction and prevents rotation of the actuating knob in an opposite second direction. For example, the handle can include a ratchet mechanism having a gear rack on the main knob and a fixed pawl that engages the gear rack to allow rotation of the main knob in a first direction as the pawl slips along teeth of the gear rack and that limits rotation of the main knob in an opposite second direction as the pawl catches a tooth on the gear rack. The pawl can be a spring-loaded machined component or alternatively, the pawl can be formed from spring leaf metal. The pawl can be configured to generate audible noise and/or at least provide tactile feedback as the pawl slips along the teeth of the gear rack. Optionally, one or more of the teeth of the gear rack can be sized and/or shaped differently from the other teeth of the gear rack to cause a distinct change in sound, e.g. pitch, or tactile feedback, e.g. clicks, resistance, that indicates to a clinician when a certain step in the deployment is achieved.

Figure 2:
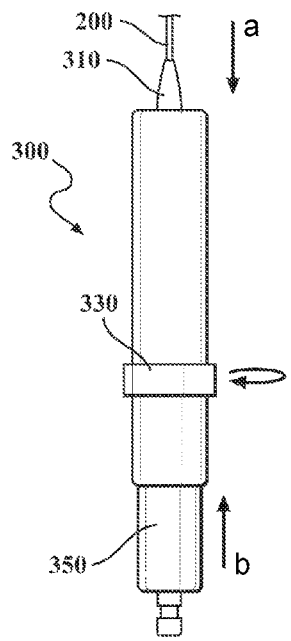
FIGS. 2-8 illustrate various states of a handle of the introducer assembly of FIG. 1.

In use, rotation of the main knob 330 about the axis 332 simultaneously operates the first actuating mechanism 320 to cause displacement of the actuating member 310 in a first direction, as indicated at arrow "a" in FIG. 2, and the second actuating mechanism 360 to cause displacement of the cover 350 in a second direction, as indicated at arrow "b" in FIG. 2. Displacement of the actuating member 310 in the first direction "a" causes corresponding displacement of the sheath 200 to allow expansion of the expandable implant 400 outwardly from the delivery configuration. The expandable vascular implant can be a self-expanding stent graft or, alternatively, a balloon-expanded implant. Displacement of the cover 350 in the second direction "b" can reveal one or more additional knobs each for operating one or more other handle functions.

Figure 3:
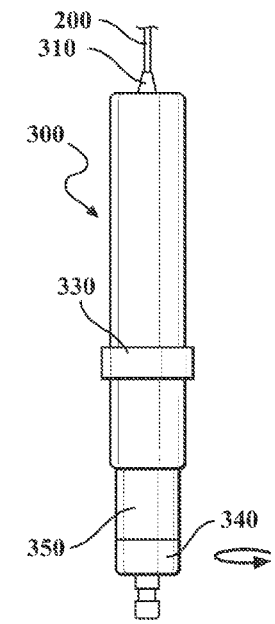

For example, as illustrated in FIG. 3, a second knob 340 is revealed after displacement of the cover 350 for operating a constraining mechanism for selectively constraining at least a portion of the implant to allow positioning of the device prior to committing to a full deployment of the implant at the treatment site. A detailed description of constraining mechanisms, construction and methods of use of such constraining mechanisms are provided in co-pending application U.S. Patent Application Publication US 2010/0049293 A1 (Zukowski et al.), the content of which is incorporated herein by reference in its entirety.

In various embodiments, the handle can be configured so that the cover can be displaced in steps to reveal additional knobs each for operating one or more other handle functions.

Figure 4:
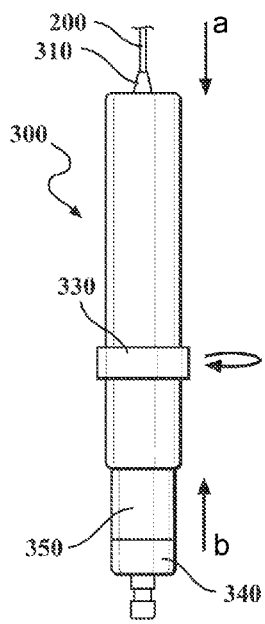
Figure 5:
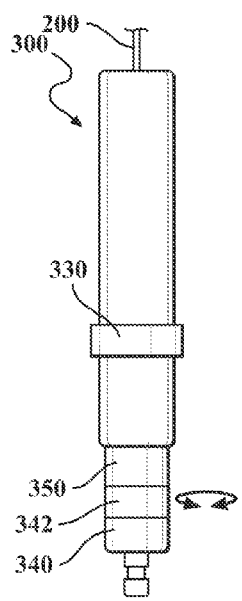

Continued rotation of the main knob 330, for example, as illustrated in FIG. 4, causes further displacement of the cover 350 in the second direction "b" to reveal a third knob 342, as shown in FIG. 5. The third knob 342 can be configured to actuate one or more other handle functions, such as displacing fibers, wires, levers, gears or any combination thereof of a steering mechanism (not shown) for selectively bending or otherwise steering at least a portion of the implant 400 during deployment.

Figure 6:
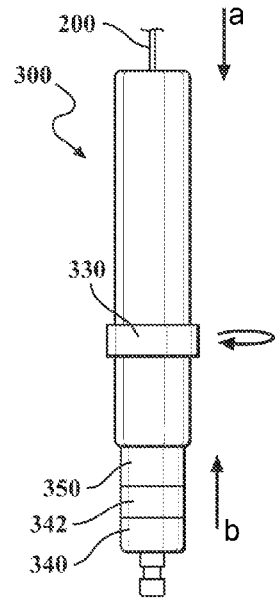
Figure 7:
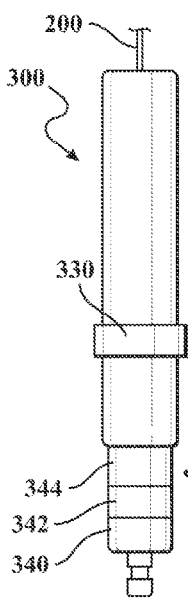
Figure 8:
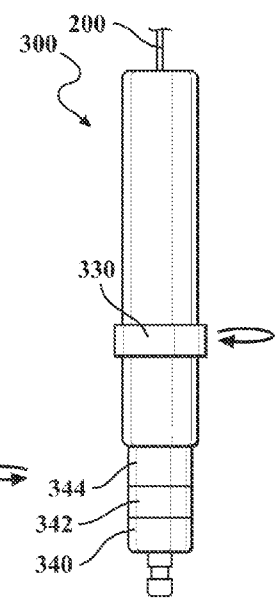

Continued rotation of the main knob 330, for example, as illustrated in FIG. 6, causes further displacement of the cover 350 in the second direction "b" to reveal a fourth knob 344, as shown in FIGS. 7-8. The fourth knob 344 can be configured to actuate one or more other handle functions, such as displacing fibers, wires, levers, gears or any combination thereof of a release mechanism. In one embodiment, a release mechanism can include a lock wire frictionally engaged with the implant to maintain a releasable coupling between the implant and the handle. The lock wire can be operatively coupled to the fourth knob to be displaced relative to and disengaged from the implant in response to actuation of the fourth knob. For example, the lock wire can be wound about a spindle portion of the fourth knob during rotation of the fourth knob. Winding of the lock wire about the spindle displaces the lock wire relative to the implant until the lock wire disengages from the implant.

In various embodiments, handle functions, such as steering, reconstraining, and deploying of an expandable implant can be operated by actuating the one or more knobs of the handle, while maintaining the implant at an intermediate configuration within a secondary or intermediate sheath or sleeve, wherein the intermediate configuration is larger than the delivery configuration and smaller than a deployed configuration. For example, the introducer assembly can include a secondary sheath for limiting expansion of the implant to an intermediate configuration after displacement of the constraining sheath. The secondary sheath can include a flexible film constraining sleeve that extends over and releasably constrains the implant. An elongated coupling member, such as a fiber or wire, stitches opposing edges or sides of the constraining sleeve together to releasably constrain the implant toward the intermediate configuration. The constraining sleeve can be opened by de-coupling the coupling member from the constraining sleeve. Further details of materials and general construction of constraining sleeves can be found in U.S. Pat. No. 6,352,561 to Leopold et al.

Figure 14:
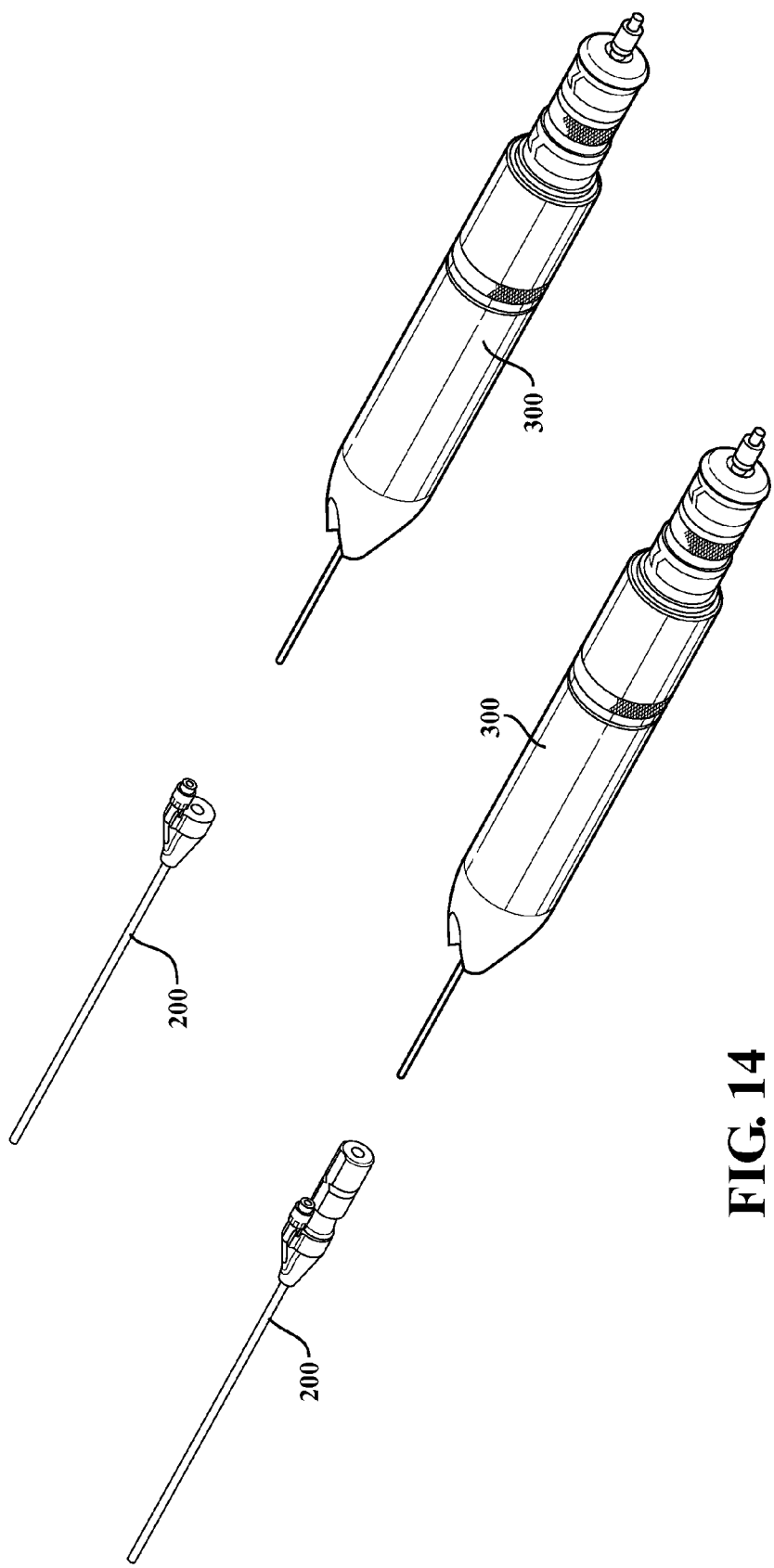
FIG. 14 illustrates perspective views of a handle and sheath of an introducer assembly decoupled from each other.

Referring to FIG. 14, the sheath 200 and handle 300 can be releasably coupled to each other for subsequent re-use of the sheath 200 as an introducer for other surgical implements after deployment of the device and de-coupling of the handle from the introducer. For example, the introducer and handle can be threaded or keyed with a slot-pin arrangement to form a releasable coupling that allows separation of the handle after deployment of the device and subsequent re-use or re-purposing of the introducer for introducing other surgical implements, such as other devices, tools, probes, cameras, drugs and saline.

Figure 15:
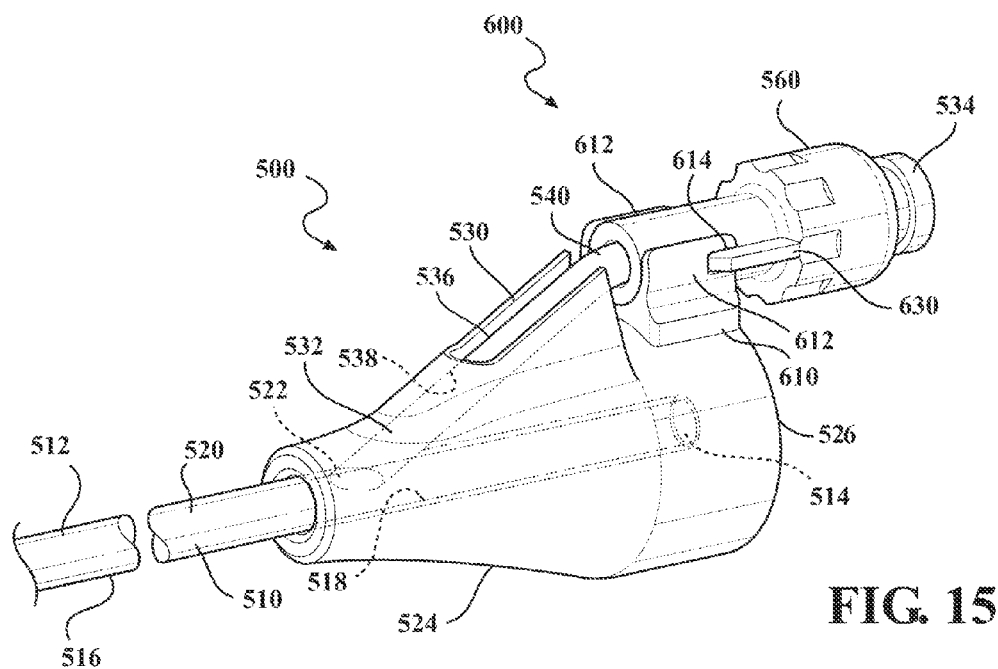
FIG. 15 is a perspective view of a portion of a catheter assembly illustrating a first catheter seated and retained by a cinching mechanism on a second catheter.
Figure 16:
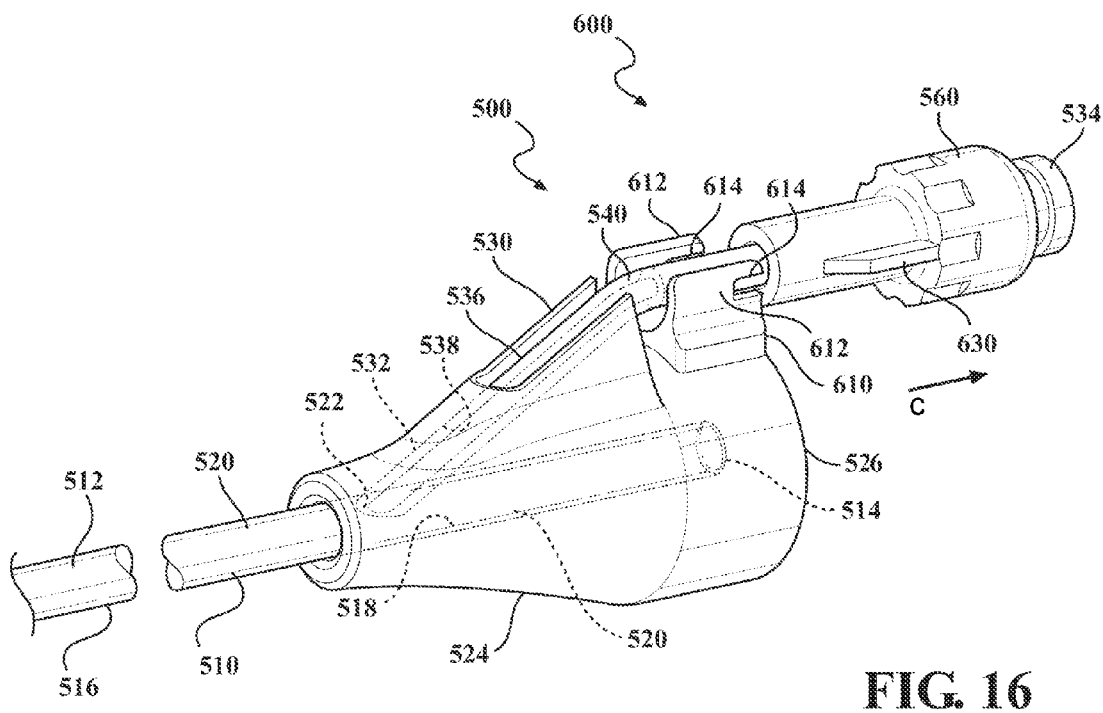
FIG. 16 is a perspective view of the catheter assembly of FIG. 15 with the second catheter unseated from the first catheter.

A catheter assembly in accordance with various embodiments can include tubular first and second catheters in fluid communication with each other, wherein the second catheter includes a port fitting and can be elastically longitudinally strained to cinch the first and second catheters together. An example of such a catheter assembly is shown in FIGS. 15-16 and generally indicated at 500. The catheter assembly 500 includes a tubular first catheter 510 having opposite first 512 and second 514 ends, an outer surface 516, and an inner surface 518 defining a lumen 520 that extends between the first 512 and second 514 ends. A side aperture 522 extends between the outer surface 516 and inner surface 518.

The catheter assembly 500 includes a first port housing 524 along the second end 514 of the first catheter 510. The first port housing 524 can include a first port 526 for accessing the lumen 520 of the first catheter 510.

The catheter assembly 500 also includes a tubular second catheter 530 having opposite first 532 and second 534 ends, an outer surface 536, and an inner surface 538 defining a lumen 540 that extends between the first 532 and second 534 ends of the second catheter 530. The first end 532 of the second catheter 530 terminates along the outer surface 516 of the first catheter 510. The lumen 540 of the second catheter 530 is in fluid communication with the lumen 520 of the first catheter 510 via the side aperture 522.

The catheter assembly 500 can include a second port housing 560 along the second end 534 of the second catheter 530. The second port housing 560 can include a second port 564 for accessing the lumen of the second catheter 530.

The catheter assembly 500 includes a cinching mechanism 600 for releasably coupling the first 510 and second 530 catheters utilizing elastic tensioning of the second catheter 530. More specifically, the cinching mechanism 600 includes a receiver 610 on the first port housing 526 that corresponds in shape and size to at least a portion of the second port housing 560 for receiving and supporting the second port housing 560 thereon. The receiver 610 includes a pair of upstanding walls 612 that are spaced apart to accommodate the second port housing 560 therebetween. At least one of the upstanding walls 612 includes a recess 614.

The cinching mechanism 600 also includes at least one protrusion 630 extending outwardly from the second port housing 560. The protrusion 630 engages the recess 614 while the second port housing 560 is seated between the upstanding walls 612 of the receiver 610, as shown in FIG. 15. In this seated state, the second catheter 530 is elastically tensioned which creates a reactive force that retains the protrusion 630 within the recess 614. The second port housing 560 can be unseated from the receiver 610 by pulling and elastically stretching the second catheter 530 along a direction generally indicated at "c" in FIG. 16 to allow the protrusion 630 to exit the recess 614. The second port housing 560 and second catheter 530 can then be freely positioned relative to the first port housing 524. The second port housing 560 can be returned to the seated state by again elastically stretching the second catheter 530, re-aligning the protrusion 630 with the recess 614 and allowing the second catheter 530 to relax, cinch and thereby maintain the second port housing 560 in the seated state in the receiver 610 of the first port housing 524.

The second catheter 530 can be made from any suitable materials that allow the second catheter 530 to be elastically stretched to create sufficient reactive force to retain the protrusion 630 in the recess 614 while the second port housing 560 is in the seated state; allow the second catheter 530 to be further elastically stretched to allow the protrusion 630 to be displaced from the recess 614 to unseat the second port housing from between the upstanding walls 612 of the receiver 610; and yet still provide conventional catheter functions, such as fluid transfer, and delivery of surgical implements and devices.

It will be apparent to those skilled in the art that various modifications and variations can be made in the present disclosure without departing from the spirit or scope of the present disclosure. Thus, it is intended that the present disclosure cover the modifications and variations of this present disclosure provided they come within the scope of the appended claims and their equivalents.

What is claimed is:

1. A catheter assembly comprising:
    a first catheter having a first end, a second end opposite the first end, an outer surface, an inner surface defining a first catheter lumen, and a side aperture;
    a second catheter having a first end, a second end opposite the first end, an outer surface, and an inner surface defining a second catheter lumen, the second catheter lumen being in fluid communication with the first catheter lumen via the side aperture in the first catheter;
    a first catheter port in fluid communication with the first catheter lumen and disposed at one of the first and second ends of the first catheter;
    a second catheter port in fluid communication with the second catheter lumen and disposed at one of the first and second ends of the second catheter; and
    a cinching mechanism including a protrusion extending from one of the first and second catheters and a recess formed in the other of the one of the first and second catheters, wherein the cinching mechanism utilizes an elastic longitudinal straining of the one of the first and second catheters to create a reactive force that retains the protrusion within the recess.

2. An introducer assembly for endoluminal delivery of vascular implants, said introducer assembly comprising:
a handle for operating functions of the introducer assembly; and
the catheter assembly as set forth in claim 1, wherein the first catheter has a first state releasably constraining a vascular implant toward a delivery configuration suitable for endoluminal delivery and a second state released to allow expansion of the vascular implant from the first configuration.

3. The introducer assembly of claim 2, wherein the catheter and handle are releasably coupled to each other.

4. The catheter assembly as set forth in claim 1, wherein the second catheter includes a port fitting and can be elastically longitudinally strained by tensioning the second catheter to cinch and couple the first and second catheters together.

5. A catheter assembly comprising:
a catheter having a first end, a second end opposite the first end, an outer surface, an inner surface defining a catheter lumen, and a side aperture;
a port tube having a first end, a second end opposite the first end, an outer surface, and an inner surface defining a port tube lumen in fluid communication with the catheter lumen, and a side aperture; and
a cinching mechanism including a protrusion extending from one of the catheter and the port tube and a recess formed in the other of the catheter and the port tube, wherein the cinching mechanism utilizes an elastic longitudinal straining of the port tube by tensioning the port tube to create a reactive force that retains the protrusion within the recess.

6. The catheter assembly as set forth in claim 5 including a first port housing through which the catheter and the port tube pass.

7. The catheter assembly as set forth in claim 6, wherein the catheter and the port tube are coupled within the first port housing.

8. The catheter assembly as set forth in claim 7, wherein the port tube extends through the first port housing and has an end terminating at a second port housing.

9. The catheter assembly as set forth in claim 8, wherein the first port housing includes a receiver that corresponds to at least a portion of the second port housing for retaining the second port housing thereon.

10. The catheter assembly as set forth in claim 9, wherein the receiver includes a pair of upstanding walls that are spaced apart for receiving the second port housing therebetween.

11. The catheter assembly as set forth in claim 10, wherein each of the pair of walls includes a recess.

12. The catheter assembly as set forth in claim 11, wherein the second port housing includes a pair of protrusions for engaging the recesses included in the pair of upstanding walls of the receiver.

13. The catheter assembly as set forth in claim 10, wherein the pair of protrusions are retained in the recesses included in the pair of upstanding walls of the receiver by the reactive force generated by elastically longitudinally straining the port tube.

* * * * *